United States Patent
Graser et al.

(10) Patent No.: US 6,319,376 B1
(45) Date of Patent: Nov. 20, 2001

(54) MEASURING PROBE

(75) Inventors: Theodor Graser; Gerhard Hoetzel; Johann Wehrmann; Heinz Eisenschmid, all of Stuttgart (DE)

(73) Assignee: Robert Bosch GmbH, Stuttgart (DE)

(*) Notice: Subject to any disclaimer, the term of this patent is extended or adjusted under 35 U.S.C. 154(b) by 0 days.

(21) Appl. No.: 09/508,257

(22) PCT Filed: Sep. 4, 1998

(86) PCT No.: PCT/DE98/02609

§ 371 Date: May 31, 2000

§ 102(e) Date: May 31, 2000

(87) PCT Pub. No.: WO99/13324

PCT Pub. Date: Mar. 18, 1999

(30) Foreign Application Priority Data

Sep. 9, 1997 (DE) .............................................. 197 39 435

(51) Int. Cl.$^7$ ................................................... G01N 27/407
(52) U.S. Cl. ........................... 204/424; 204/426; 204/428
(58) Field of Search ..................................... 204/421–429

(56) References Cited

U.S. PATENT DOCUMENTS

| | | |
|---|---|---|
| 4,956,072 | 9/1990 | Kojima et al. . |
| 5,246,562 | * 9/1993 | Weyl et al. . |
| 5,329,806 | * 7/1994 | McClanahan et al. . |
| 5,900,129 | * 5/1999 | Tsuji et al. . |

FOREIGN PATENT DOCUMENTS

| | | |
|---|---|---|
| 0 624 791 | 1/1993 | (EP) . |
| 63 259453 | 2/1989 | (JP) . |

* cited by examiner

Primary Examiner—T. Tung
(74) Attorney, Agent, or Firm—Kenyon & Kenyon

(57) ABSTRACT

A sensor, particularly for determining the oxygen content in exhaust gasses of internal combustion engines, includes sensor element which is fixed in a metallic housing and a sealing flange which is integrally formed on the housing and rests on a sealing seat which is formed on an exhaust system. The sealing flange has two ring elements which are integrally formed on the housing and each have an inclined sealing surface, a hollow space being formed between the two ring elements inside the housing.

8 Claims, 2 Drawing Sheets

MEASURING PROBE

FIELD OF THE INVENTION

The present invention relates to a sensor, particularly for determining the oxygen content in exhaust gasses of internal combustion engines.

BACKGROUND INFORMATION

European Patent No. EP 624 791 (corresponding to U.S. Pat. No. 5,329,806) describes a gas sensor where a sensor element is fixed in a tubular, metallic housing in a gas-tight manner. At its lower part, the tubular housing has a lip facing radially outward which forms a sealing flange. The gas sensor is mounted in an opening of an exhaust system, the lip sitting on a sealing seat formed in the opening. A banjo bolt is led over the housing and screwed into a thread arranged in the opening, thereby joining the lip to the exhaust system in a gas-tight manner. Problematic in this design is, however, that the pressing or upsetting of the relatively thin-walled material of the housing can produce microcracks at the lip which can cause the leakiness of the housing.

SUMMARY OF THE INVENTION

The present invention has the advantage over the related art that the sealing flange is absolutely gas-tight, and the inclined sealing surfaces produce an absolutely gas-tight sealing seat at the exhaust pipe. Moreover, the hollow design of the sealing flange produces a spring effect which also supports the sealing effect.

It is particularly advantageous for the inclined sealing surfaces to be designed in an angle between 10° and 30°, preferably of 20°. Arranging the sealing flange behind the sealing arrangement for the sensor element, as viewed from the measuring gas side, has an advantageous effect on the installation of the sensor. In this manner, the sensor element can first be equipped with the ceramic parts of the sealing arrangement. The housing is then slipped over the sensor element equipped with the sealing arrangement. Furthermore, it is expedient to attach a connecting piece to the exhaust pipe, the connecting piece, at the end face, forming a sealing seat for the sealing flange.

DETAILED DESCRIPTION

Figure 1:
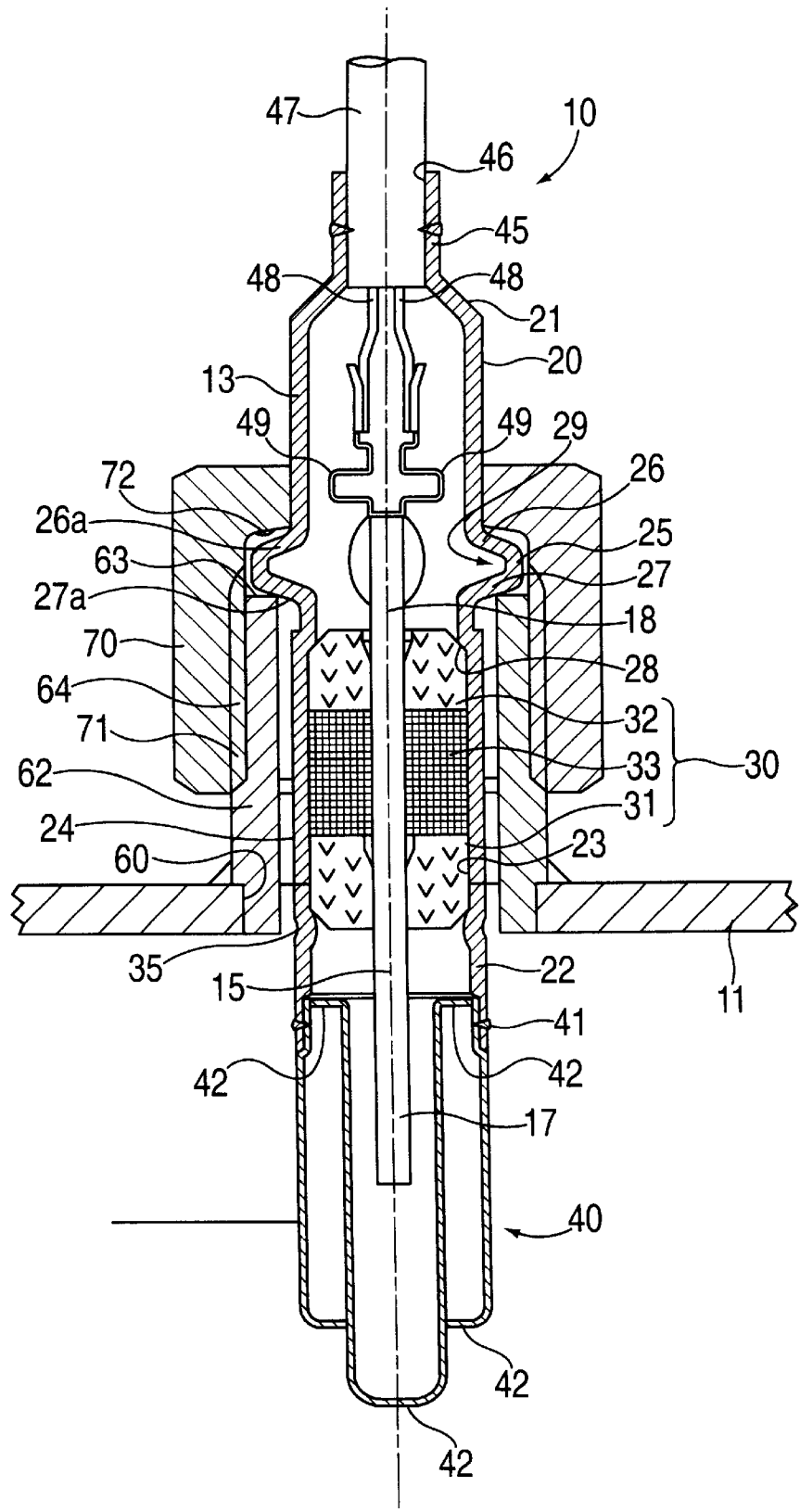
FIG. 1 shows a longitudinal cross section through a sensor mounted in an exhaust pipe.

A sensor 10, for example, an electrochemical oxygen sensor, is mounted in an exhaust pipe 11 and has a metallic housing 13, in which a planar sensor element 15 having a section 17 on a measuring gas side and a section 18 on a connection side is arranged.

Figure 2:
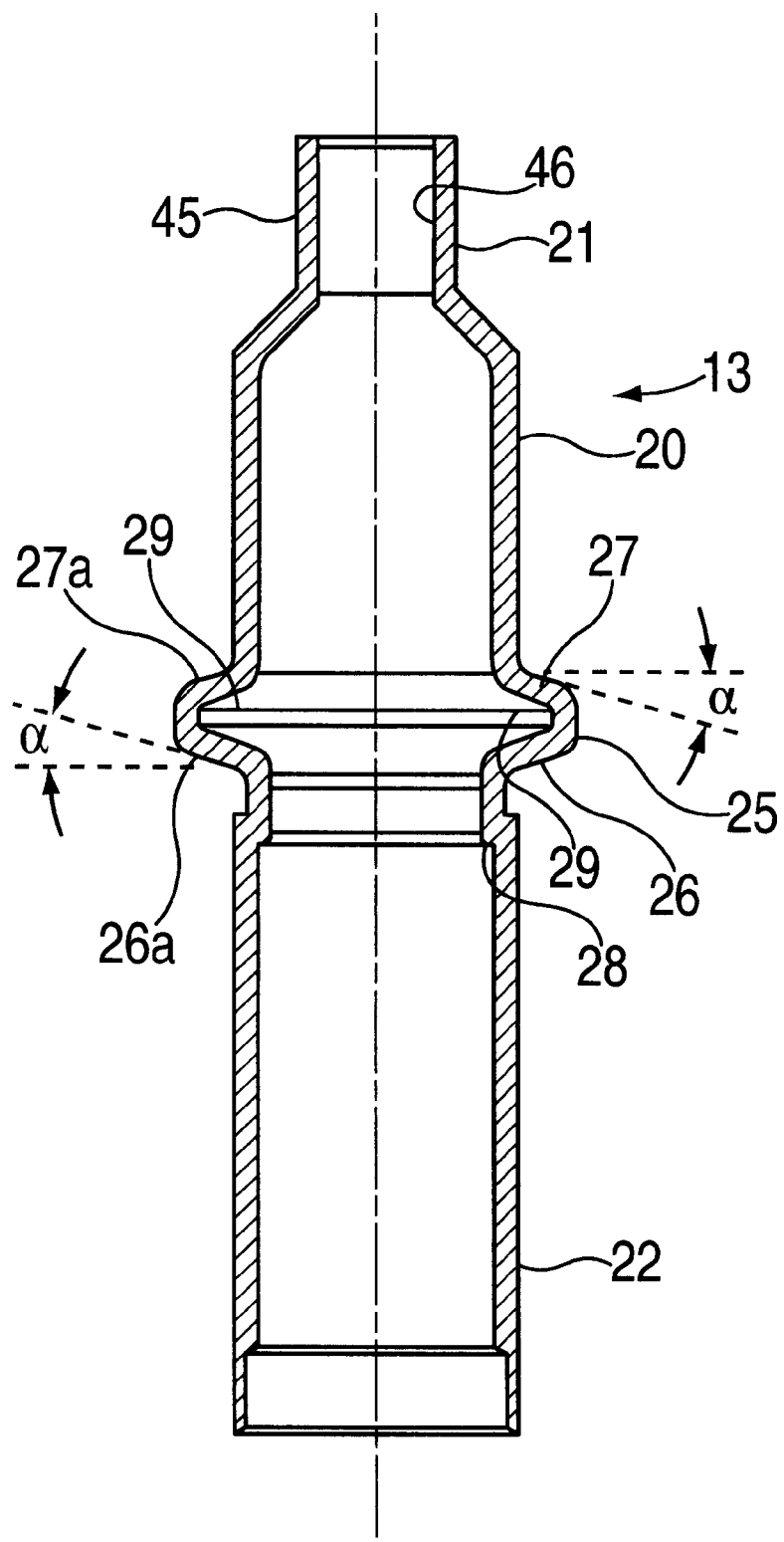
FIG. 2 shows a detailed longitudinal cross section through the housing of the sensor according to FIG. 1.

Housing 13 is a pipe element 20 which is open on both sides and has a end section 21 on connection side and an end section 22 on measuring gas side as well as an interior wall 23 and an exterior wall 24. Moreover, pipe element 20 has a radially surrounding sealing flange 25 having an upper ring element 26 with a downward inclined upper sealing surface 26a, and having a lower ring element 27 with an upward inclined lower sealing surface 27a. The two sealing surfaces 26a and 27a run at an angle a of approximately 20° relative to a plane running at right angles to the center line of pipe element 20 (FIG. 2). Sealing flange 25 having ring elements 26, 27 running toward one another is designed in such a manner that a hollow space 29 forms inside housing 13 between ring elements 26, 27. In this manner, the two ring elements 26, 27 can act as resilient legs whereby the sealing effect of sealing surfaces 26a, 27a is increased. In front of sealing flange 25, as viewed from the measuring gas side, an annular surface 28 is integrally formed on interior wall 23, the annular surface constituting a stop face for a sealing arrangement 30 which will be described later. Because of this design, sealing flange 25 is located behind sealing arrangement 30, as viewed form the measuring gas side and is consequently relatively far away from exhaust pipe 11.

To form sealing flange 25, pipe element 20 is, for example, initially upset, a rounded bulge forming at pipe element 20 in the process. This bulge is subsequently processed, for example, by the manufacturing process of rotary kneading in such a manner that the two inclined sealing surfaces 26a, 27a are formed. However, one can also conceive other manufacturing processes by which sealing flange 25 can be manufactured efficiently, for example, by drawing and subsequently upsetting.

Sealing arrangement 30 mounted in housing 13 is composed, for example, of a molded ceramic part 31 on measuring gas side, a molded ceramic part 32 on connection side, and a sealing element 33 arranged in between. Molded ceramic parts 31 and 32 are composed, for example, of $Al_2O_3$ and each have penetrations, which are not further described, for sensor element 15. Sealing element 33 is composed, for example, of steatite and is inserted in a prepressed condition, having a penetration for sensor element 15, as well. First, housing 13 is slid over sealing arrangement 30 until annular surface 28 strikes against molded ceramic part 32 on connection side. Subsequently, molded ceramic part 31 on measuring gas side is acted upon by a stamp on measuring gas side, using a pressure force rated such that prepressed sealing element 33 is squashed so that the power components press both against sensor element 15 and interior wall 23. While the force is acting upon molded ceramic part 31 on measuring gas side, a contraction in area 35 running radially and facing inward is formed in pipe element 20 at end section 22 on measuring gas side. In this manner, ceramic part 31 on measuring gas side is kept in the pressing position with respect to sealing element 33.

At end section 22 on measuring gas side, sensor element 15 protrudes from housing 13 and is surrounded there, for example, by a double protective tube 40. Double protective tube 40 is inserted into end section 22 on measuring gas side, and there joined to housing 13 by a surrounding weld 41. Double protective tube 40 has gas entrance and outlet apertures 41 for the exhaust gas/measuring gas. In the present exemplary embodiment, double protective tube 40 is formed in one piece.

End section 21 on connection side of housing 13 has a tapering section 45 with an opening 46. Welded in opening 46 is, for example, a metallic jacketed tube 47. Arranged in jacketed tube 47 are connecting cables 48 for sensor element 15. Connecting cables 48 are connected to contacting pieces 49 which are contacted to terminals (not further shown), which are arranged at section 18 on connection side of sensor element 15. Sensor element 15 can be contacted, for example, by clamping or by an integral connection. However, the cables may be brought out through opening 46 with the assistance of a temperature-resistant PTFE cable gland, as well.

For fasting sensor 10 in exhaust pipe 11, an opening 60 is provided in exhaust pipe 11, a cylindrical connecting piece 62 having a plane annular surface 63 and a threaded section 64 being welded into the opening. Lower sealing surface 27*a* of sealing flange 25 rests on annular surface 63. A union nut 70 having an internal screw thread 71 and an internal annular surface 72 is led over housing 13. Union nut 70 is screwed on connecting piece 62, thereby pressing sealing flange 25 on annular surface 63. Thus, annular surface 63 constitutes a sealing seat for sealing flange 25.

For fasting sensor 10 in exhaust pipe 11, however, other forms of fastening means are also possible, for example, fastening with the assistance of a banjo bolt having a thread on the outer surface which is screwed into an internal screw thread arranged on connecting piece 62, the sealing seat for sealing flange 25 having to be designed with an additional annular surface inside connecting piece 62. It is also conceivable to interposition an adaptor between connecting piece 62 and the banjo bolt, sensor 10 then, with sealing flange 25, sitting on an annular surface of the adaptor, and the adaptor, with a further annular surface, resting on the annular surface of connecting piece 62.

What is claimed is:

1. A sensor for determining an oxygen content in an exhaust gas of an internal combustion engine, comprising:

a housing;

a sensor element fixed in the housing; and a sealing flange formed out of a material of the housing, the sealing flange including two ring elements formed out of the housing, each of the two ring elements having an inclined sealing surface, a hollow space being formed between the two ring elements inside the housing, the two ring elements acting as resilient legs.

2. The sensor according to claim 1, wherein the sealing surfaces are slanted at an angle of 10° to 30° relative to a plane running at right angles to a center line of the housing, the housing being tubular-shaped.

3. The sensor according to claim 2, wherein the angle is about 20°.

4. The sensor according to claim 1, further comprising a sealing arrangement for the sensor element mounted in the housing, the sealing flange being situated behind the sealing arrangement, as viewed from a measuring gas side of the sensor.

5. The sensor according to claim 4, wherein the housing further comprises two annular surfaces, a first of the two annular surfaces being further from a measuring gas than a second of the two annular surfaces, the sealing arrangement being pressed between the two annular surfaces.

6. The sensor according to claim 1, further comprising a connecting piece encircling an opening in an exhaust pipe in a gas-tight manner, a sealing seat for the sealing flange being formed on the connecting piece.

7. The sensor according to claim 1, further comprising a fastening element for mounting the housing in an exhaust pipe.

8. Exhaust pipe for an internal combustion engine with a sensor for determining an oxygen content in an exhaust gas of the internal combustion engine in the exhaust pipe, comprising:

a pipe with an opening;

a cylindrical connecting piece, the cylindrical connecting piece having a plane annular section, the cylindrical connecting piece being welded into the opening;

a housing;

a sensor element fixed in the housing; and a sealing flange formed out of a material of the housing, the sealing flange including two ring elements formed out of the housing, each of the two ring elements having an inclined sealing surface, a hollow space being formed between the two ring elements inside the housing, the two ring elements acting as resilient legs;

the sealing flange resting on the plane annular section of the cylindrical connecting piece.

* * * * *